(12) United States Patent
Tobias et al.

(10) Patent No.: US 10,499,884 B2
(45) Date of Patent: Dec. 10, 2019

(54) SYSTEM AND METHOD FOR SCANNING FOR A SECOND OBJECT WITHIN A FIRST OBJECT USING AN ADAPTIVE SCHEDULER

(71) Applicant: White Eagle Sonic Technologies, Inc., Santa Clara, CA (US)

(72) Inventors: Richard Tobias, San Jose, CA (US); Bicheng Wu, Palo Alto, CA (US); Ashish Parikh, Los Altos, CA (US)

(73) Assignee: White Eagle Sonic Technologies, Inc., Santa Clara, CA (US)

( * ) Notice: Subject to any disclaimer, the term of this patent is extended or adjusted under 35 U.S.C. 154(b) by 102 days.

(21) Appl. No.: 14/098,464

(22) Filed: Dec. 5, 2013

(65) Prior Publication Data

US 2014/0171798 A1 Jun. 19, 2014

Related U.S. Application Data

(60) Provisional application No. 61/745,792, filed on Dec. 25, 2012, provisional application No. 61/734,067, (Continued)

(51) Int. Cl.
*A61B 8/00* (2006.01)
*G01S 7/52* (2006.01)
(Continued)

(52) U.S. Cl.
CPC ............ *A61B 8/54* (2013.01); *G01S 7/52082* (2013.01); *G01S 7/52085* (2013.01); (Continued)

(58) Field of Classification Search
CPC combination set(s) only.
See application file for complete search history.

(56) References Cited

U.S. PATENT DOCUMENTS

| 4,287,768 A | 9/1981 | Hayakawa et al. |
| 4,572,202 A | 2/1986 | Thomenius |

(Continued)

FOREIGN PATENT DOCUMENTS

| CN | 1179298 A | 4/1998 |
| CN | 1646064 A | 7/2005 |

(Continued)

OTHER PUBLICATIONS

PCT: Notification of Transmittal of the International Search Report and the Written Opinion of the International Searching Authority, or the Declaration dated Feb. 24, 2014 for International Application No. PCT/US2013/073554, International Filing Date Dec. 6, 2013.

(Continued)

*Primary Examiner* — Peter Luong
(74) *Attorney, Agent, or Firm* — Womble Bond Dickinson (US) LLP

(57) ABSTRACT

Method for scanning for second object on or within first object starts by receiving information on first object and second object. Task lists are generated that include at least one task action based on information on first object and second object. Based on task lists, beamer is then signaled to generate and send first signal to first probe unit to perform first beam firing. Receiver processes first data signal from first probe unit that is then analyzed to determine if first object is identified using processed first data signal. Upon determination that first object is identified, based on task list, beamer is signaled to generate and send second signal to second probe unit to perform second beam firing. Receiver processes second data signal from second probe unit that is then analyzed to determine if second object is identified using processed second data signal. Other embodiments are described.

25 Claims, 4 Drawing Sheets

Related U.S. Application Data filed on Dec. 6, 2012, provisional application No. 61/734,291, filed on Dec. 6, 2012, provisional application No. 61/745,794, filed on Dec. 25, 2012.

(51) Int. Cl.
  *G01S 15/89* (2006.01)
  *A61B 8/08* (2006.01)
  *A61B 8/06* (2006.01)
  *A61B 8/14* (2006.01)

(52) U.S. Cl.
  CPC ........ *G01S 7/52098* (2013.01); *G01S 15/899* (2013.01); *A61B 8/06* (2013.01); *A61B 8/08* (2013.01); *A61B 8/14* (2013.01); *A61B 8/4218* (2013.01); *A61B 8/4444* (2013.01); *A61B 8/5207* (2013.01); *G01S 15/8979* (2013.01)

(56) References Cited

U.S. PATENT DOCUMENTS

| | | | |
|---|---|---|---|
| 4,993,417 | A | 2/1991 | Seo |
| 5,119,342 | A | 6/1992 | Harrison, Jr. et al. |
| 5,121,361 | A | 6/1992 | Harrison, Jr. et al. |
| 5,140,192 | A | 8/1992 | Nogle |
| 5,641,908 | A | 6/1997 | Hayakawa |
| 5,680,865 | A * | 10/1997 | Tanaka .................... 600/441 |
| 5,709,209 | A | 1/1998 | Friemel et al. |
| 5,787,889 | A | 8/1998 | Edwards et al. |
| 5,795,297 | A * | 8/1998 | Daigle ............... G01S 15/899 600/447 |
| 5,797,846 | A | 8/1998 | Seyed-Bolorforosh et al. |
| 5,919,138 | A | 7/1999 | Ustuner |
| 5,921,932 | A | 7/1999 | Wright et al. |
| 5,928,152 | A | 7/1999 | Wright et al. |
| 6,029,116 | A | 2/2000 | Wright et al. |
| 6,124,828 | A | 9/2000 | Champeau |
| 6,126,601 | A | 10/2000 | Gilling |
| 6,126,607 | A | 10/2000 | Whitmore, III et al. |
| 6,402,693 | B1 | 6/2002 | Emery |
| 6,436,049 | B1 | 8/2002 | Kamiyama et al. |
| 6,438,401 | B1 | 8/2002 | Cheng et al. |
| 6,459,925 | B1 | 10/2002 | Nields et al. |
| 6,468,212 | B1 | 10/2002 | Scott et al. |
| 6,526,163 | B1 | 2/2003 | Halmann et al. |
| 6,567,687 | B2 | 5/2003 | Front et al. |
| 6,585,651 | B2 | 7/2003 | Nolte et al. |
| 6,666,833 | B1 | 12/2003 | Friedman et al. |
| 6,714,667 | B1 | 3/2004 | Mooney et al. |
| 6,839,762 | B1 | 1/2005 | Yu et al. |
| 6,980,419 | B2 | 12/2005 | Smith et al. |
| 7,022,075 | B2 | 4/2006 | Grunwald et al. |
| 7,043,063 | B1 | 5/2006 | Noble et al. |
| 7,069,425 | B1 | 6/2006 | Takahashi |
| 7,115,093 | B2 | 10/2006 | Halmann et al. |
| 7,117,134 | B2 | 10/2006 | Dubois et al. |
| 7,280,473 | B2 | 10/2007 | Wu et al. |
| 7,347,820 | B2 | 3/2008 | Bonnefous |
| 7,450,130 | B2 | 11/2008 | Swedberg et al. |
| 7,514,069 | B2 | 4/2009 | Achilefu et al. |
| 7,536,535 | B2 | 5/2009 | Wood |
| 7,648,461 | B2 | 1/2010 | Thiele et al. |
| 7,691,063 | B2 | 4/2010 | Peteresen et al. |
| 7,846,099 | B2 | 12/2010 | Lin et al. |
| 7,850,912 | B2 | 12/2010 | Favuzzi et al. |
| 7,981,039 | B2 | 7/2011 | Peteresen et al. |
| 7,991,986 | B2 | 8/2011 | Yamamoto et al. |
| 8,057,390 | B2 | 11/2011 | Witte et al. |
| 8,081,806 | B2 | 12/2011 | Friedman et al. |
| 8,096,949 | B2 | 1/2012 | Chen et al. |
| 8,167,803 | B2 | 5/2012 | McMorrow et al. |
| 8,226,560 | B2 | 7/2012 | Arai et al. |
| 8,226,563 | B2 | 7/2012 | Peteresen et al. |
| 8,246,545 | B2 | 8/2012 | Hastings |
| 8,248,885 | B2 | 8/2012 | Ma et al. |
| 8,287,471 | B2 | 10/2012 | Liu et al. |
| 8,289,284 | B2 | 10/2012 | Glynn et al. |
| 2002/0177878 | A1 | 11/2002 | Poore et al. |
| 2002/0198454 | A1 | 12/2002 | Seward et al. |
| 2003/0045795 | A1 | 3/2003 | Bjaerum et al. |
| 2003/0135712 | A1 | 7/2003 | Theis |
| 2004/0006272 | A1* | 1/2004 | Vortman et al. ............ 600/443 |
| 2004/0019447 | A1 | 1/2004 | Shachar |
| 2004/0250050 | A1 | 12/2004 | Ludden et al. |
| 2004/0254465 | A1 | 12/2004 | Sano et al. |
| 2005/0074154 | A1 | 4/2005 | Georgescu et al. |
| 2005/0075566 | A1 | 4/2005 | Satoh |
| 2006/0004606 | A1 | 1/2006 | Wendl et al. |
| 2006/0058673 | A1 | 3/2006 | Aase et al. |
| 2006/0116578 | A1 | 6/2006 | Grunwald et al. |
| 2006/0288194 | A1 | 12/2006 | Lewis et al. |
| 2007/0255139 | A1 | 11/2007 | Deschinger et al. |
| 2007/0258631 | A1 | 11/2007 | Friedman et al. |
| 2007/0258632 | A1 | 11/2007 | Friedman et al. |
| 2007/0259158 | A1 | 11/2007 | Friedman et al. |
| 2007/0260861 | A1 | 11/2007 | Kaabouch et al. |
| 2008/0033292 | A1 | 2/2008 | Shafran |
| 2008/0077820 | A1 | 3/2008 | Jensen et al. |
| 2008/0126639 | A1 | 5/2008 | Oakes et al. |
| 2008/0146922 | A1 | 6/2008 | Steins et al. |
| 2008/0242993 | A1 | 10/2008 | Shin |
| 2008/0249407 | A1 | 10/2008 | Hill et al. |
| 2008/0249410 | A1 | 10/2008 | Okuno |
| 2008/0300487 | A1 | 12/2008 | Govari et al. |
| 2009/0012394 | A1 | 1/2009 | Hobelsberger et al. |
| 2009/0043195 | A1 | 2/2009 | Poland |
| 2009/0089555 | A1 | 4/2009 | Cataldo et al. |
| 2009/0138318 | A1 | 5/2009 | Hawkins et al. |
| 2009/0187099 | A1 | 7/2009 | Burcher |
| 2010/0016719 | A1 | 1/2010 | Freiburger et al. |
| 2010/0017750 | A1 | 1/2010 | Rosenberg et al. |
| 2010/0023886 | A1 | 1/2010 | Shin et al. |
| 2010/0312113 | A1 | 12/2010 | Ogasawara et al. |
| 2010/0324420 | A1* | 12/2010 | Snook ..................... A61B 8/00 600/443 |
| 2011/0201900 | A1 | 8/2011 | Zhang et al. |
| 2011/0288413 | A1 | 11/2011 | Baba et al. |
| 2012/0092527 | A1 | 4/2012 | Lavin et al. |
| 2012/0157842 | A1* | 6/2012 | Davis et al. .................. 600/439 |
| 2012/0157843 | A1 | 6/2012 | Lavin et al. |
| 2013/0116561 | A1* | 5/2013 | Rothberg ............ A61B 8/4254 600/438 |
| 2013/0251221 | A1 | 9/2013 | Harrison |
| 2013/0263511 | A1 | 10/2013 | Agam et al. |

FOREIGN PATENT DOCUMENTS

| | | |
|---|---|---|
| EP | 0829735 A2 | 3/1998 |
| WO | 2012123942 A1 | 9/2012 |

OTHER PUBLICATIONS

U.S. Appl. No. 14/098,569 Office Action dated Nov. 4, 2015.
U.S. Appl. No. 14/098,472 Office Action dated Nov. 30, 2015.
U.S. Appl. No. 14/098,469 Final Office Action dated May 18, 2016.
U.S. Appl. No. 14/098,472 Final Office Action dated May 23, 2016.
Extended Search Report for European Application No. EP13860141 dated Jun. 29, 2016.
Office Action for U.S. Appl. No. 14/098,452 dated Nov. 22, 2016.
Office Action for U.S. Appl. No. 14/098,459 dated Nov. 23, 2016.
Office Action for U.S. Appl. No. 14/098,472 dated Aug. 26, 2016.
Firsts Office Action for CN Application No. 201380071646.2 dated Sep. 28, 2016.
Office Action for U.S. Appl. No. 14/098,472 dated Mar. 28, 2017.
"Corrected Notice of Allowance for U.S. Appl. No. 14/098,444 dated Nov. 25, 2016", Nov. 25, 2016.
"Notice of Allowance for Chinese Application No. 201380071646.2 dated Nov. 10, 2017", Nov. 10, 2017.
"Notice of Allowance for U.S. Appl. No. 14/098,444 dated Aug. 22, 2016", Aug. 22, 2016.
"Notice of Allowance for U.S. Appl. No. 14/098,452 dated May 24, 2017", May 24, 2017.

(56) References Cited

OTHER PUBLICATIONS

"Notice of Allowance for U.S. Appl. No. 14/098,459 dated Jan. 24, 2018", Jan. 24, 2018.
"Notice of Allowance for U.S. Appl. No. 14/098,469 dated Aug. 15, 2016", Aug. 15, 2016.
"Notice of Allowance for U.S. Appl. No. 14/098,472 dated May 21, 2018", May 21, 2018.
"Office Action for Chinese Application No. 201380071646.2 dated Apr. 28, 2017", Apr. 28, 2017.
"Office Action for U.S. Appl. No. 14/098,444 dated Mar. 25, 2016", Mar. 25, 2016.
"Office Action for U.S. Appl. No. 14/098,452 dated Feb. 5, 2016", Feb. 5, 2016.
"Office Action for U.S. Appl. No. 14/098,452 dated Jun. 16, 2016", Jun. 16, 2016.
"Office Action for U.S. Appl. No. 14/098,459 dated Jul. 11, 2016", Jul. 11, 2016.
"Office Action for U.S. Appl. No. 14/098,459 dated Jun. 8, 2017", Jun. 8, 2017.
"Office Action for U.S. Appl. No. 14/098,459 dated Mar. 8, 2016", Mar. 8, 2016.
"Office Action for U.S. Appl. No. 14/098,472 dated Nov. 1, 2017", Nov. 1, 2017.
"Office Action for U.S. Appl. No. 15/684,714 dated Apr. 12, 2018", Apr. 12, 2018.
"Supplemental Notice of Allowance for U.S. Appl. No. 14/098,459 dated Feb. 8, 2018", Feb. 8, 2018.

* cited by examiner

SYSTEM AND METHOD FOR SCANNING FOR A SECOND OBJECT WITHIN A FIRST OBJECT USING AN ADAPTIVE SCHEDULER

CROSS-REFERENCED AND RELATED APPLICATIONS

This application claims the benefit pursuant to 35 U.S.C. 119(e) of U.S. Provisional Application No. 61/745,792, filed on Dec. 25, 2012, which application is specifically incorporated herein, in its entirety, by reference.

This application claims the benefit pursuant to 35 U.S.C. 119(e) of U.S. Provisional Application No. 61/734,067, filed on Dec. 6, 2012, which application is specifically incorporated herein, in its entirety, by reference.

This application claims the benefit pursuant to 35 U.S.C. 119(e) of Provisional U.S. Application No. 61/734,291, filed on Dec. 6, 2012, which application is specifically incorporated herein, in its entirety, by reference.

This application claims the benefit pursuant to 35 U.S.C. 119(e) of Provisional U.S. Application No. 61/745,794, filed on Dec. 25, 2012, which application is specifically incorporated herein, in its entirety, by reference.

TECHNICAL FIELD

Embodiments of the invention generally relates to ultrasound scanning and particularly to ultrasound scanning using a plurality of beams to scan (or search for) a second object in or on a first object using an adaptive scheduler.

BACKGROUND

Today's ultrasound systems have limited, fixed functionality and require sophisticated user control. Most ultrasound systems cannot provide multiple simultaneous functions. The ultrasound systems that can provide multiple simultaneous functions have the functions as fixed functions that are not flexible to user demands or need for adaptation. Accordingly, in these systems, a selection between different functions may be available, however, no deviations that relate, for example, to timing of the fixed functions is possible. For example, in the case of ultrasound systems, it may be possible to have a Doppler beam and a B-mode beam. The combined functions, resulting from the use of the different beams, are provided as preprogrammed solutions. These solutions are selected, for example, by using a touch of a button. However, there is no flexibility provided to the user of the system for changes that require the reconfiguring and reshuffling of the timed scheduled actions that are included in the preprogrammed solutions.

Moreover, some current imaging systems allow for combinations of, for example, a photoacoustic and ultrasound imager. These imaging systems use hardware counters to divide a clock to generate timing pulses for a transducer that supports both photoacoustic and ultrasound events. However, these imaging systems provide little in the form of flexibility to adapt to needs of modern ultrasound imaging that may require changes that befit a specific imaging situation. Other imaging systems provide ways for continuous interleaving of, for example, ultrasound beams. However, such interleaving is limited in its flexibility and being able to address the needs of future ultrasound imaging.

An operator of these current ultrasound apparatuses is required to be skilled in the operation of the machine. For example, the operator needs to be trained and capable of directing beams to the desired bodily object to be tested. Thus, the operator is required to know how to appropriately move the probes used to achieve a desired image. As a result of the requirement to have highly skilled personnel to operate the current ultrasound systems, whether in medical applications or others, use of the current ultrasound systems is limited by the availability of such highly skilled personnel. Furthermore, even for a skilled operator, it might prove a challenge to perform some of the more complicated ultrasound actions (e.g., locate an object on or within another object).

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. In the drawings.

DETAILED DESCRIPTION

Figure 1:
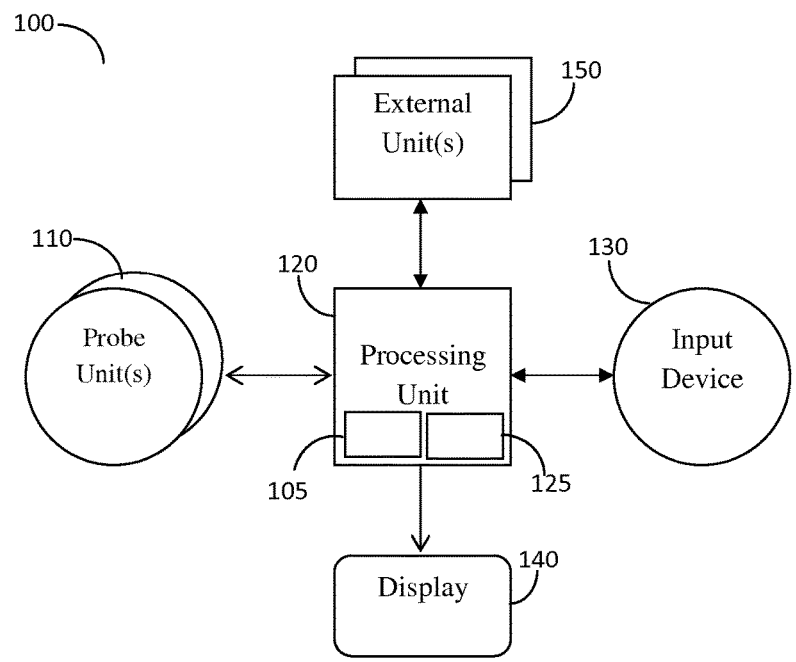
FIG. 1 shows an ultrasound system including an adaptive scheduler for executing ultrasound system actions in real time according to an embodiment of the invention.

In the following description, numerous specific details are set forth. However, it is understood that embodiments of the invention may be practiced without these specific details. In other instances, well-known circuits, structures, and techniques have not been shown to avoid obscuring the understanding of this description.

In the description, certain terminology is used to describe features of the invention. For example, in certain situations, the terms "component," "unit," "module," and "logic" are representative of hardware and/or software configured to perform one or more functions. For instance, examples of "hardware" include, but are not limited or restricted to an integrated circuit such as a processor (e.g., a digital signal processor, microprocessor, application specific integrated circuit, a micro-controller, etc.). Of course, the hardware may be alternatively implemented as a finite state machine or even combinatorial logic. An example of "software" includes executable code in the form of an application, an applet, a routine or even a series of instructions. The software may be stored in any type of tangible machine-readable medium.

A sophisticated ultrasound system supports multiple simultaneous functions such as imaging, blood flow measurement and heartbeat monitoring. The ultrasound system performs these functions by executing sequences of actions such as firing beams, receiving beam data, and moving mechanical arms. These actions frequently have rigorous real-time requirements. The ultrasound system performs functions by executing one or more parallel tasks, where each task requires a sequence of actions. The ultrasound system cannot perform conflicting actions at the same time. Accordingly, in some embodiments, actions conflict if they require the same resource, e.g., the same transmitter, the same receiver or the same area of memory. In other embodiments, actions conflict if the ultrasound beams from two different transmitters travel through the same area of the target and make it impossible for a receiver to identify the source.

Further, some actions depend on events that cannot be accurately predicted. For example, the system may need to wait for a mechanical arm to complete its movement before it fires the next beam. The system must wait for a laser to be charged before it can fire a laser beam. The time taken to charge a laser varies significantly and cannot be predicted to the required accuracy. The ultrasound system indicates the completion of mechanical movement or laser charging by signaling events. Thus, some actions may depend on asynchronous events.

Accordingly, in some embodiments, the ultrasound system supports changes to the list of parallel tasks. For instance, a human user may view an ultrasound image and request new functions to be performed. An automated system may change the list of tasks in response to analysis of the ultrasound results. In some embodiments, the automated system uses the adaptive scheduler to schedule actions from the updated task list. Scheduling the actions may include signaling to a processor to send commands to other units to perform the actions. The adaptive scheduler may be implemented in hardware, software, firmware or any combination thereof as discussed below. In prior ultrasound systems, a skilled human operator is required to analyze results and modify ultrasound parameters. For example, an ultrasound operator may wish to locate a human heart valve, monitor the heart rate and measure the shape of the heart valve movement. In one embodiment of the invention, the automated system employs analysis procedures to monitor the ultrasound results. The analysis procedures may be implemented using software. The automated system employing the analysis procedures determines the required task-list changes and signals an appropriate event to the adaptive scheduler. The automated system employing the analysis procedures causes the modification of the task-list while searching for the heart valve that is to be found within a human heart. The automated system employing the analysis procedures causes new tasks to start when the ultrasound system locates the heart valve. Thus, the ultrasound system needs to respond to events that change the task list (e.g., when it receives an event indicating that the heart valve is located resulting from employing the analysis procedures, or as an input from the end user). In this example, the event may be a signal received by the adaptive scheduler that indicates that the heart valve is located. The signal may be a single bit digital signal wherein the high signal ('1') may indicate that the heart valve is located.

Accordingly, in one embodiment of the invention, the adaptive scheduler further described below handles the scheduling of task actions. Each task to be performed may include a plurality of task actions. For instance, a task to be performed by the ultrasound system may be measuring the blood flow within a particular blood vessel. Hence, there is a first scheduled task for finding the particular blood vessel and a separate task for measuring the blood flow. It should be further noted that the adaptive scheduler may have to switch between the tasks if the focus on the particular blood vessel is lost, for example, due to a motion of the patient or the probe. The task actions included in the task of measuring the blood flow may include: firing one of the beams, and collecting the data (e.g., ultrasound data) from the beam. The adaptive scheduler adapts the schedule of task actions to ensure that actions do not conflict. When adapting the schedule of task actions, if actions are found to conflict, in one embodiment, the adaptive scheduler ensures that high priority actions are handled prior to lower priority actions. The adaptive scheduler handles events. The events may be signals received by the adaptive scheduler that indicate the completion of certain tasks or task actions. For example, when an external unit (e.g., robot arm) has completed the movement required, the event received may be a signal that indicates that the external unit has completed the movement. The events may also be a signal received from an input device that indicates that a list of tasks has been inputted by the user. In some embodiments, events can cause the adaptive scheduler to pause task actions, modify task parameters, add or delete tasks and to invoke procedures, such as analysis procedures in hardware or software or any combination thereof, for locating a heart valve. In other embodiments, in response to events, the adaptive scheduler sends a signal to the processor to send commands to probe units or external units to start executing a task action. For instance, in response to receiving an event that indicates that data has been collected from a first beam associated with a higher priority, the adaptive scheduler may signal to the processor to send a start command to the second beam of a lower priority. In some embodiments, the adaptive scheduler sends the commands to the probe units or external units instead of the processor.

In some embodiments, a system and method search for an object on or within another object using an adaptive scheduler. Information associated with the object that is on or within the second object is received and data signals associated with a plurality of beam firings associated with the information is also received. An adaptive scheduler is used to arrange the plurality of beam firings within a task list that includes a plurality of task actions. The task actions may be associated with plurality of beam firings, respectively, and may be organized in a schedule. The schedule may be a time wheel that includes a plurality of slot positions. The adaptive scheduler may arrange the beam firings in the slot positions such that the conflicting events do not interfere with each other.

FIG. 1 shows an ultrasound system including an adaptive scheduler for executing ultrasound system actions in real time according to an embodiment of the invention. As shown in FIG. 1, the ultrasound system 100 may include an adaptive scheduler 105. In one embodiment, the adaptive scheduler 105 is coupled to one or more probe units 110. Each probe unit 110 typically controls one or more transducers embodied therein. The transducers typically contain multiple elements capable of transmitting and receiving ultrasound beams. In one embodiment, the adaptive scheduler 105 is part of a processing unit 120 that handles user interactions, image display and system control. In one embodiment, the adaptive scheduler 105 is implemented as a software procedure executing on a processor. In some embodiments, the adaptive scheduler 105 includes a dedicated processor that is only used for adaptive scheduling. In a second embodiment the adaptive scheduler 105 is implemented in hardware. For instance, the adaptive scheduler 105 may include application-specific integrated circuit (ASIC) and/or field-programmable gate array (FPGA). The processing unit 120 may include a microprocessor, a micro-controller, a digital signal processor, or a central processing unit, and other needed integrated circuits such as glue logic. The term "processor" may refer to a device having two or more processing units or elements, e.g. a CPU with multiple processing cores. The processing unit 120 may be used to control the operations of the adaptive scheduler 105. For example, the processing unit 120 may executes software to control the adaptive scheduler 105 (e.g. to transmit and receive data to other components of system 100 (e.g., external units 150, probe unit 110). In some cases, a particular function may be implemented as two or more pieces of software that are being executed by different hardware units of a processor.

In one embodiment, the processing unit 120 sends probe control commands, telling the probe units 110 when to fire specific beams and when to collect data. Such operation, as explained in further detail herein below, is performed, for example, from a memory 125 containing instructions that are executed by the processing unit 120. A memory 125 may also be included in the adaptive scheduler 105. The memory 125 that may include one or more different types of storage such as hard disk drive storage, nonvolatile memory, and volatile memory such as dynamic random access memory. The memory 125 may also include a database that stores data received from the probe units 110 and the external units 150. The memory 125 may also store instructions (e.g. software; firmware), which may be executed by the processing unit 120. As multiple operations of the ultrasound system may be needed (e.g., firing beams at various times), a task list is generated and altered by the adaptive scheduler 105 to address the combination of actions that are desired by the user of the system 100, further described herein. This embodiment of the invention provides for flexibility that is not achievable in prior art systems. The processing unit 120 is configured to further retrieve data collected by a probe unit 110 data. The processing unit 120 takes input commands from one or more input devices 130. The input devices 130 may be a keyboard, mouse, or touch screen that allows a user to input commands.

The input devices 130 typically provide high-level commands to the processing unit 120 which in turn, under control of the embedded instruction memory 125 performs at least the tasks described in greater detail herein below. The processing unit 120 may output at least a result respective of the data collected to, for example, a display unit 140 that is coupled to the processing unit 120. A display unit 140 may be replaced or augmented by a storage unit (not shown) to allow the storing of the collected data for future use. The display unit 140 may show an image, a video comprised of a series of image frames, text, as well as combinations thereof.

While a single adaptive scheduler is referenced herein the use of a plurality of adaptive schedulers is possible without departing from the scope of the invention. As discussed above, the adaptive scheduler may be implemented in hardware, for example through a configurable circuit, or in memory of the system 100, where the memory is loaded with instructions, which when executed by the processor, causes the processor to perform methods of adaptively scheduling the task actions or cause the processor to control the adaptive scheduler, or adaptive schedulers. In one embodiment, cycle accurate timing for the firing of the beams is provided by the system 100 based, at least in part on the directions or signals received from the adaptive scheduler. In some embodiments, the adaptive scheduler may be used to configure at least a probe unit.

In an embodiment, the ultrasound system 100 may control one or more external units 150, such as lasers, robot arms and motors. The external units 150 may also require time synchronization with probe units 110 operations. In one embodiment, the processing unit 120 sends external units 150 control commands based on the adaptive scheduler 105's selected task action as further explained below. For example, the processing unit 120 may send a control command telling a robot arm (e.g., external unit 150) to move a probe upon receipt of a signal from the adaptive scheduler 105 that received an event indicating that a unit of data has been collected.

The ultrasound system 100 may receive a specification of ultrasound system tasks and events through, for example, input devices 130. The ultrasound system 100 generates a task identifying a sequence of task actions. Some of the task actions may have real-time constraints and some may depend on events. For instance, some task actions may not start until an event is received by the adaptive scheduler 105. For example, the task action may be to move a robot arm which cannot begin until an event is received that indicates that the data from a beam is finished being collected. In one embodiment, the ultrasound system 100 computes the time needed to complete each task action in the specification received. The ultrasound system 100 generates a list of the task actions using a linked list in memory 125. In some embodiments, the specification may include tasks and events that are associated with multiple beam firings of different types. A beam firing task action may require a setup time which is the amount of time needed to configure the transducer before firing a beam. The setup time may depend on the transducer. Different beam firing types are called modes. Switching modes (for example, switching from B-Mode mode to color-flow Doppler) typically requires a mode switching delay. The switching delay acts as an additional setup time. Each beam firing task action has a firing time, also known as pulse duration, which is the amount of time that the transducer outputs ultrasound waves. The firing time depends of the beam type and the purpose of the beam firing. For instance, a shorter firing time can give a better quality image. Doppler beams have a longer firing period than B-Mode beams. Each beam also has a collection time, which is the time needed to receive the reflected or pass-through ultrasound waves. The ultrasound propagation time depends on the medium through which the beam passes. The collection time depends on the depth of the scan. The ultrasound system 100 may need to distinguish the source of the collected data. Accordingly, the ultrasound system 100 may avoid two beams firing at the same time. A "dead-time" time interval between data collection and the next beam firing may also be introduced as needed.

Some beam types have a pulse repetition period which is the time between successive firings. Successive firings lead to the construction of a single image. Repeating this sequence of firings can generate multiple images. The ultrasound system 100 may, for instance, have a requirement to generate 60 images per second. Doppler beams have a pulse repetition period whereas B-mode scan beams do not.

Some beam firings need to be consecutive in time. Using multi-focal-zones allows the ultrasound system 100 to get significantly better image quality. The ultrasound system 100 scans with beams focused at different distances. The ultrasound system 100 may scan with the first beam focused at 0-5 centimeters (cm), a second beam focused at 5-10 cm and a third beam focused at 10-15 cm. The data collected from the three different levels may be combined to form one line of an image. This beam firing sequence can be repeated using different collectors to generate a complete image. The ultrasound system 100 may need to schedule the actions that generate a single line consecutively.

In one embodiment, the processing unit 120 receives an input specification including a list of tasks (or task list) to be performed that includes ultrasound tasks and external unit tasks. Each ultrasound task may include, for example: the beam type, the number of beam firings, the setup time, the firing time, the dead-time, the pulse repetition period, the desired images per second rate, the number of multi-focal zones, and other timing constraints. Each external unit function (e.g., an external unit task) may include, for example: desired external unit task actions and the desired external unit task actions' timing constraints. The desired external unit task action may be for example a movement of a robot arm. The processing unit 120 or the adaptive scheduler 105 processes each task description and produces a list of sequential task actions such as beam firing actions and data collection actions. The task list may also include a plurality of tasks that are associated with a plurality of beams of differing priority levels. In some embodiments, the plurality of tasks includes at least one of a photoacoustic laser firing task and an electrocardiogram (ECG) task.

In one embodiment, the processing unit 120 creates a schedule of timing actions ("task list") and selects a task action following the method described herein. It should be understood that the processing unit 120, in one embodiment, may schedule the dependent or independent operation of a plurality of probe units 110 coupled to the probe interface 230 such that their beam firing is either dependent or independent of each other. Each of the probe units 110 may have, for example, its own task list of ultrasound actions that may be adaptively modified by the adaptive scheduler 105. In another embodiment, a single task list that may be adaptively modified by the adaptive scheduler may be used to cause the firing of beams by at least one of the plurality of probe units 110. Similarly, a plurality of external units 150 may be coupled to the probe interface 230 illustrated in FIG. 2, or in one embodiment, a dedicated interface (not shown) used to couple a plurality of external devices 150 to the processing unit 120. In one embodiment, the adaptive scheduler 105 may use one or more task lists to cause the operation of the one or more probe units 110 and the one or more external units 150. These operations being performed independent or dependent of each other. As discussed above, the ultrasound system 100 may receive a specification of ultrasound system tasks and events through, for example, a feedback resulting from measurements made by the system 100 or from input devices 130 (e.g., a change requested by a user of the system 100 by entering an input). These changes may occur in real-time as the system 100 executes the task list including the tasks that may include tasks and task actions that were earlier entered to the system 100. It should be further understood that task actions included in the task lists may be added as well as removed in real-time by the adaptive scheduler 105 and the task actions included in the task lists may also be added and removed when the system 100 is off-line for reconfiguration.

Figure 2:
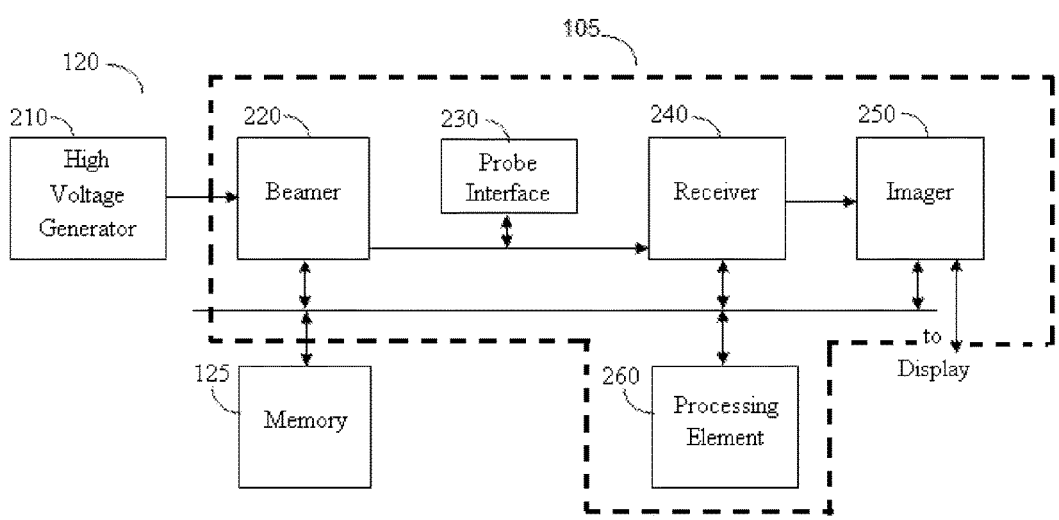
FIG. 2 shows a block diagram representation of the details of the processing unit of the ultrasound system according to an embodiment of the invention.

FIG. 2 shows a block diagram representation of the details of the processing unit of the ultrasound system according to an embodiment of the invention. In this embodiment, the processing unit 120 comprises a high voltage generator 210, the memory 125 and the adaptive scheduler 105. The adaptive scheduler 105 may comprise a beamer 220, a probe interface 230, a receiver 204, an imager 250 and a processing element 260. In some embodiments, the adaptive scheduler 105 also includes the high voltage generator 210 and the memory 125. In the embodiment in FIG. 2, the high voltage generator 210 is coupled to the beamer 220 and provides the high voltage necessary for the proper operations of at least the probes 110. In one embodiment, the probes 110 may be coupled to the processing unit 120 through probe interface 230 which is coupled to the beamer 220. In one embodiment, the beamer 220 generates control signals that control different functions of the probes 110 (e.g., controls the firing of their beams). The beamer 220 may also generate the high voltage transmission signals that are converted by transducers included in the probe 110 into the ultrasound signals that are fired by the probes 110. The beamer 220 may provide the control signals and/or the high voltage transmission signals to the probes 110 via the probe interface 230. In one embodiment, the probe interface 230 is also used to interface to the external units 150. As shown in FIG. 2, the probe interface 230 may further coupled to a receiver 240. The receiver 240 may receive and shape or process data signals from at least one of the probe units 110 into a usable form. For instance, the probe unit 110 generates ultrasound signals that are fired onto an object (e.g., human body) and the "bounce back" signal from the object is received by the probe unit 110. The "bounce back" signal is transmitted from the probe unit 110 to the receiver 240 via the probe interface 230. The receiver 240 may then shape and process the data signal from the probe unit 110 (e.g., the "bounce back" signal) and may provide the shaped data signals to an imager 250. In some embodiments, the receiver 240 may shape or process the signals by analog-to-digital conversion or by performing noise reduction or noise filtering. The receiver 240 may also receive and shape or process data signals from at least one of the external units 120. Thus, the imager 250 may be coupled to the receiver 240 and to a display 140. The imager 250 may generate display signals based on the data signals received from the receiver 240. The display signals may then be transmitted from the imager 250 to the display 140 to be displayed as an image, text and/or video. In other embodiments, the receiver 240 may further provide the data signals from the probe unit 110 to the processing element 260 to analyze the data signals and assess whether the next task action in the task list can start. For example, the probe unit 120 may transmit a data signal to the adaptive scheduler 105 via the probe interface 230, the data signal may be processed by the receiver 240 and provided to the processing element 260 that analyzes the shaped data signal and determines that the shaped data signal provides the results of a B-Mode beam firing which indicates that the task action of beam firing from the B-Mode beam is completed. Accordingly, in this example, the processing element 260 of the adaptive scheduler 105 determines that beam having a lower priority than the B-Mode beam may start its task action without interfering with the B-Mode beam's task actions. As illustrated in FIG. 2, the beamer 220, the receiver 240 and the imager 250 are coupled to the processing element 260 (e.g., processor, a digital signal processor, microprocessor, application specific integrated circuit, a micro-controller, etc.) that may further be coupled to a memory 125. The memory 125 contains instructions that when executed by the processor element 260 cause the processing unit 120 (or the processor element 260) to control the adaptive scheduler 105 to adaptively schedule the tasks performed by the system 100 as described herein. For instance, the execution of the instructions stored in memory 125 may cause the processor element 260 to (i) signal to the beamer 220 to generate signals that cause the probes 110 to fire their beams and to provide the signals to the probes 110 via the probe interface 230, (ii) configure the receiver 240 to receive data signals from the probe 110 and/or the external units 120, and (iii) signal to the imager 250 to generate display signals based on the data signals received from the receiver 240. In another embodiment, as discussed above, the instructions stored in the memory 125 may be executed by a processor that is included in the processing unit 120 that is separate from the adaptive scheduler 105. The memory 125 may be further used to store data at least images generated by the imager 250. In one embodiment, the processing unit 120 may be implemented as a monolithic integrated circuit (IC) which may or may not include certain elements thereof. For example, high voltage generator 210 may be implemented off-chip. Furthermore, the system 120 may be implemented in whole or in part on a monolithic IC, including but not limited to a system-on-chip (SoC) implementation.

The following embodiments of the invention may be described as a process, which is usually depicted as a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a procedure, etc. and implemented in hardware, software or firmware, and any combination thereto.

Figure 3:
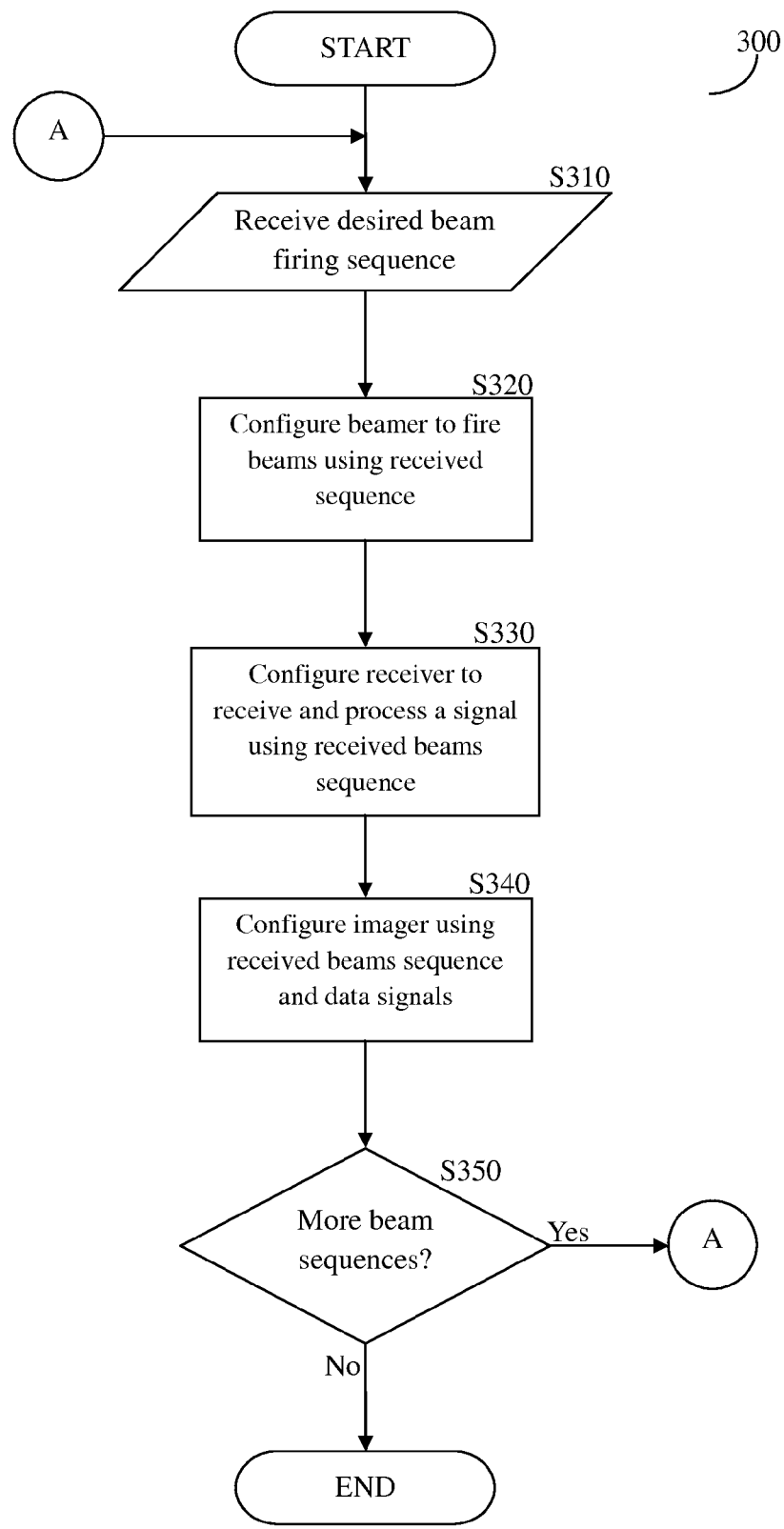
FIG. 3 shows a flowchart of an example method for adaptively scheduling ultrasound system actions by the processing unit according to an embodiment of the invention.

FIG. 3 shows a flowchart of an example method for adaptively scheduling ultrasound system actions by the processing unit according to an embodiment of the invention. The method 300 in FIG. 3 starts at S310 with the adaptive scheduler 105 receiving a desired sequence of beam firing, (e.g., the sequence of timed beam firings may be included in a task list). For example, the adaptive scheduler 105 may receive a sequence of beam firings required for an ultrasound imaging session that may include Doppler and B-mode beams. The adaptive scheduler 105 may check if there are any events that require it to add new tasks to the task list, may checks if there are any events that require it to delete tasks from the task list, and while the adaptive scheduler 105 iterates over the task list, it determines if it could start the next task action of the selected task. For instance, the sequence of beam firing received may cause the adaptive scheduler 105 to add task actions (e.g., the plurality of beam firings identified in the sequence of beam firing) to the task list or delete task actions (e.g., lower priority task actions that conflict with the higher priority beam firings included in the beam firings identified in the sequence of beam firing) from the task list. While the adaptive scheduler 105 iterates over the task list, it determines if it could start each of the plurality of beam firings. In one embodiment, the adaptive scheduler 105 determines that it cannot start a first beam firing if the first beam firing conflicts with a second beam firing of higher priority.

In S320, a beamer, for example beamer 220, is configured using the received sequence of beam firing. In one embodiment, the beamer generates signals based on the received sequence of beam firing and provides the signals to the respective probes 110 via the probe interface 230. This allows the system 100 to fire the beams as configured by the adaptive scheduler 105. In S330, a receiver, for example receiver 240, is configured using the received sequence of beam firing. This allows the system 100 to receive data signal that is associated with the beams that are identified in the sequence of beam firing. In one embodiment, the data signal is received from the probes used to fire the beams identified in the sequence of beam firing. The receiver 240 may also be configured using the received sequence of beam firing to shape the signals by analog-to-digital conversion or by performing noise reduction. In S340, if necessary, an imager, for example imager 250, is configured using the received sequence of beam firing and the received data signal from the receiver 240, to generate an image for display. In S350, the adaptive scheduler 105 may check whether there are additional beam sequences to be received and if so, the method 300 proceeds with execution at S310. If the adaptive scheduler 105 determines that no additional beam sequences are to be received, the method 300 terminates.

In one embodiment, the external devices 150 may also be similarly configured to enable the operation of the system 100. In this embodiment, the adaptive scheduler 105 may provide signals to the respective external devices 105 via the probe interface 230 in accordance with the task list received. The task list may include task actions to be performed by the external devices (e.g., moving a mechanical arm). In this embodiment, the receiver 240 may receive data signals that are associated with the external devices that are identified in the task list. These data signals may also be received from the external devices that are identified in the task list via the probe interface 230. It should be further understood that the system 100 may be dynamically configured. For example, by analyzing an image and/or a received signal, the adaptive scheduler 105 may generate a modified or otherwise new sequence of desired beam firing included in a task list. This modified or new sequence being generated may then automatically alter the operations of the system 100.

Figure 4:
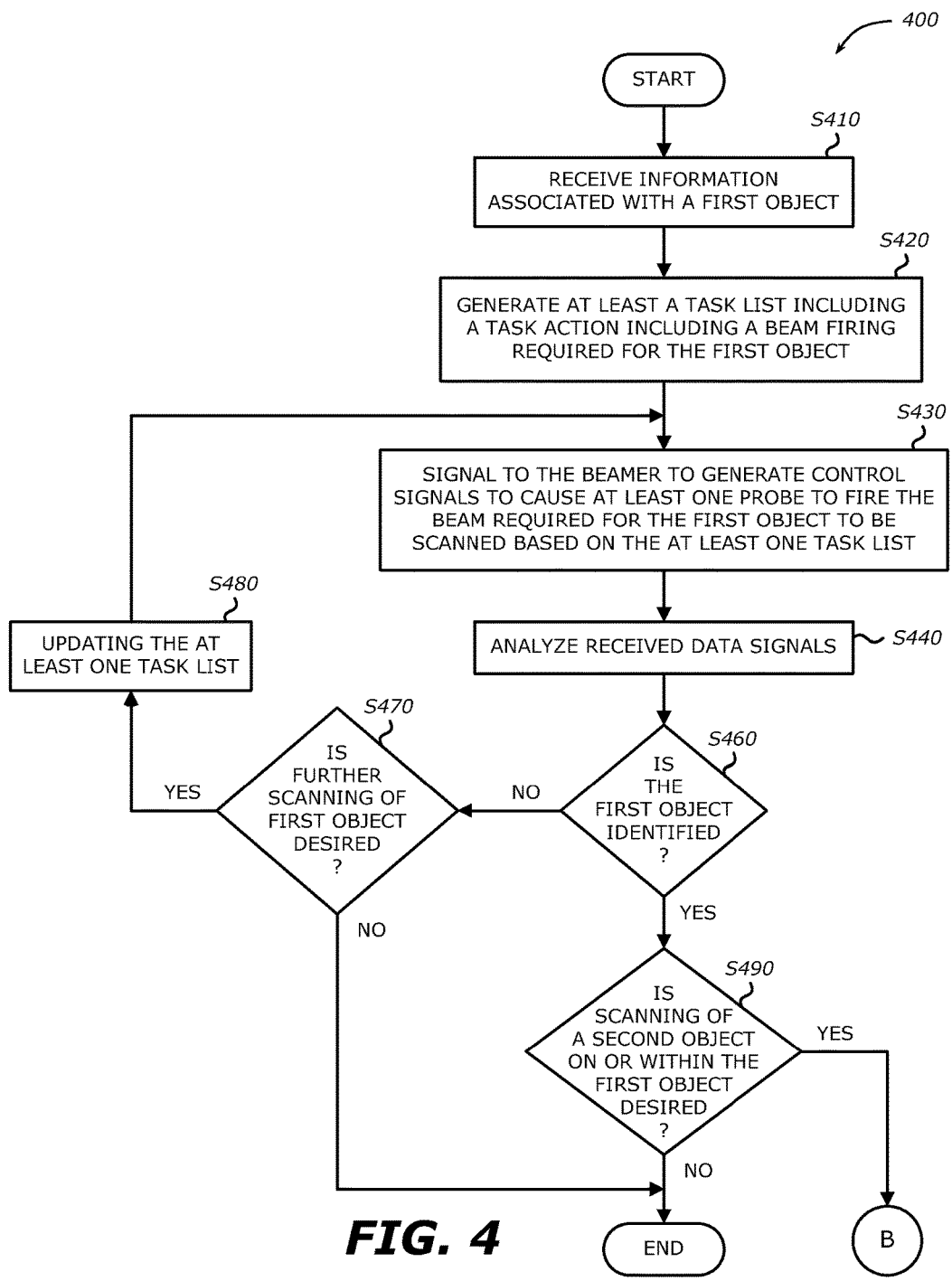
FIG. 4 shows a flowchart of an example method for automatically adjusting beams to scan a first object according to an embodiment of the invention.

FIG. 4 shows a flowchart of an example method 400 for automatically adjusting beams to scan a first object according to an embodiment of the invention. In S410, the processing element 260 of the adaptive scheduler 105 receives information associated with a first object to be scanned. The first object may be, for example, an organ within a human body. The information may include a speckle type, which is indicative of the physical nature of the object. Based on the different speckle types, it is possible to differentiate one live tissue from another. In S420, the processing element 260 generates at least one task list that includes at least one task action based on the information received. The task action may include a beam firing required for the first object to be scanned. In one embodiment, one or more beam types may be used, as well as one or more probe types. In one embodiment, the plurality of probes may perform a generic search scan. Furthermore, a portion of the results obtained from each of the plurality of probes may be used to generate a picture. It is also possible to select only a number of probes to be used for generating an image. In one embodiment, some of the probes may be used for image generation, while other probes may be used for enabling measurements or Doppler scans. In S430 the processing element 260, based on the task list, signals to the beamer 220 to generate signals that are sent to at least one probe unit 120 to fire the beams required for the first object to be scanned. In S440, the processing element 260 via the receiver 240 receives data signals from the at least one probe unit 120 that fired the beams required for the first object to be scanned. As discussed above, the receiver 240 may shape and process the "bounce back" signals from at least one probe unit 120 and provide the processed "bounce back" signals (e.g., data signals) to the processing element 260. In S450, the processing element 260 analyzes the data signals to determine if the scan of the first object has been completed. In one embodiment, the processing element 260 determines that the scan of the first object has been completed when the processing element 260 can identify the first object using the data signals. In one embodiment, to determine if the first object is identified includes determining whether the received information on the first object corresponds to the data signals. Accordingly, in S460, the processing element 260 determines whether the first object was identified and if so, the process 400 continues with S490. Otherwise, if the processing element 260 does not determine that the first object was identified, the process 400 continues with S470. In S470, the processing element 260 determines whether scanning of the first object is desired and should continue. In one embodiment, the processing element 260 automatically determines that scanning of the first object should continue when the first object cannot be identified using the data signals. The process 400 continues with S480 if the scanning of the first object is determined to continue at S470, and the process 400 terminates if the scanning of the first object is determined not to continue at S470. In one embodiment, in S470, when the processing element 260 checks whether further scanning of the first object is desired and should continue, the processing element 260 may check whether the user inputted instructions to adjust the probes, or terminate the process 400. The decision to perform one or more attempts to scan for the first object may also be under full control of the user, or performed semi-automatically, or performed fully automatically by the processing element 260. In S480, using the analyzed information in S450 and the information associated with the first object received at S410, an updated one or more task lists are generated by the processing element 260 and the process 400 continues with S430. The updated one or more task lists may include task actions that are updated to adjust the beams firings required to scan the first object. The updated one or more task lists may also include informing the user that the first object was not found. At S490, the processing element 260 determines whether scanning of a second object on or within the first object is desired. If no scanning of a second object is desired, the process 400 terminates and if scanning of a second object is desired, the process 400 may continue as shown in FIG. 5.

Figure 5:
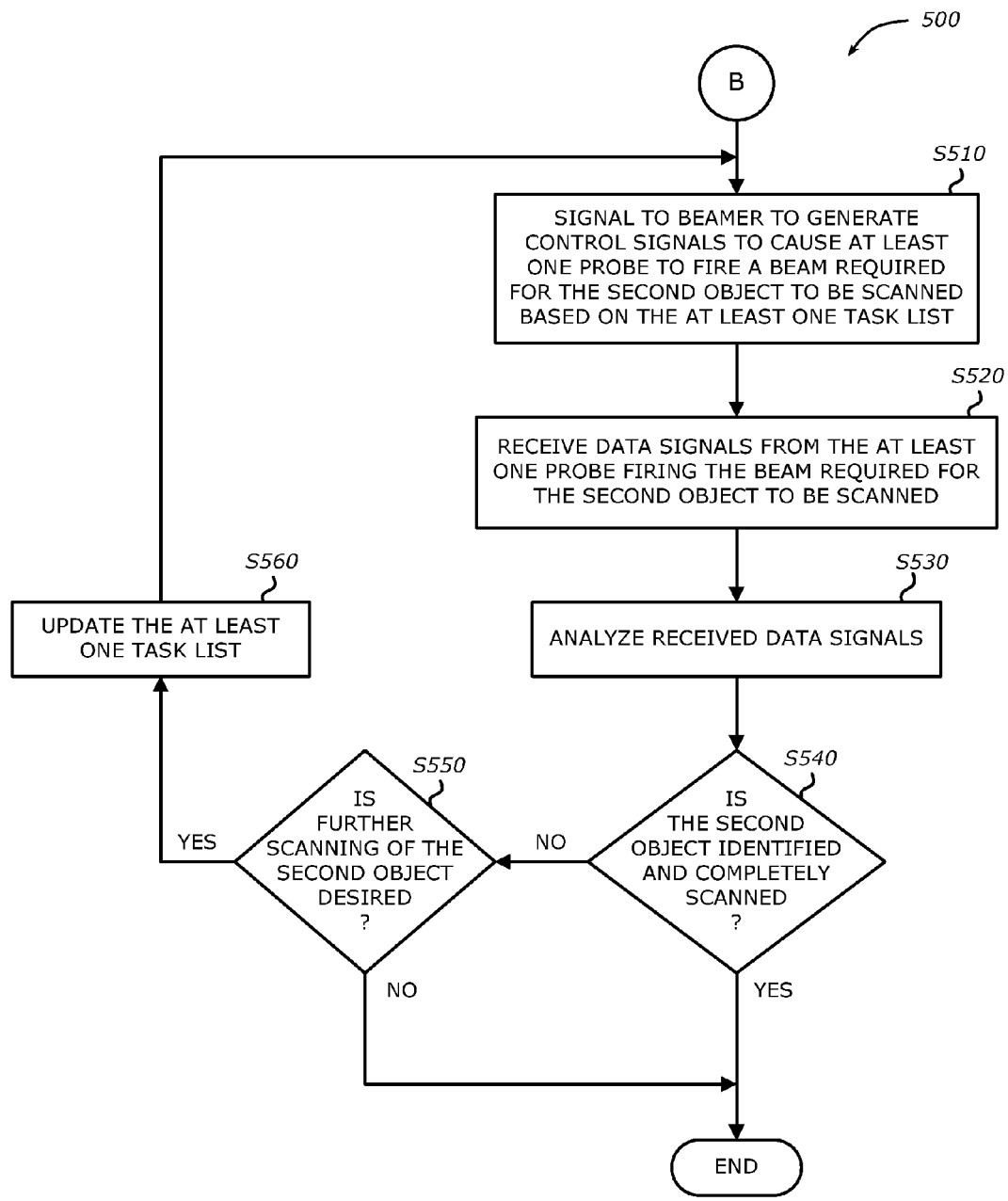
FIG. 5 shows a flowchart of an example method for automatically adjusting beams to scan a second object on or within a first object according to an embodiment of the invention.

FIG. 5 shows a flowchart of an example process 500 for automatically adjusting beams to scan a second object on or within a first object according to an embodiment of the invention. In this embodiment, the process 500 continues from S490 in FIG. 4 when it is determined that the first object has been identified and scanning of the second object is desired. For example, the first object may be a heart and the second object may be a mitral valve of the heart. In this embodiment, at S410, the information received includes information on the heart (first object) and information on the mitral valve (second object). The information associated with the second object may also be included in the information associated with the first object that was received in S410. Further, in this embodiment, at S420, the at least one task list that is generated may further comprise a task action that includes a beam firing required for the second object. In another embodiment, a second task list may be generated that is different from the task list generated by the processing element 460 comprising a task action that includes a beam firing required for the first object. At S510, the processing element 260 signals to the beamer to generate signals to cause at least one probe to fire a beam required for the second object to be scanned based on the at least one task list. The at least one probe firing the beam required for the second object to be scanned may be the same as or different from the at least one probe firing the beam required for the first object to be scanned. At S520, the processing element 260 receives data signals from the at least one probe firing the beam required for the second object to be scanned. At S530, the processing element 260 analyses the received data signals. At S540, the processing element 260 determines whether the second object is identified and completely scanned. If so, the process 500 terminates. If the processing element 260 determines that the second object is not identified or not completely scanned, the processing element 260 determines whether further scanning is desired. As above for the first object in S470, the decision to perform one or more attempts to scan for the second object may also be under full control of the user, or performed semi-automatically, or performed fully automatically by the processing element 260. In one embodiment, to determine if the second object is identified includes determining whether the received information on the second object corresponds to the data signals received from the receiver in response to the beam firing required to scan the second object If no further scanning for the second object is desired at S550, the process 500 ends. If further scanning of the second object is desired at S550, the process 500 continues to S560. At S560, the processing element 260 updates the at least one task list. The updated one or more task lists may include task actions that are updated to adjust the beams firings required to scan the second object. The updated one or more task lists may also include informing the user that the second object was not found. Once the at least one task list is updated in S560, the process 500 returns to S510.

An embodiment of the invention may be a machine-readable medium having stored thereon instructions which program a processor to perform some or all of the operations described above. A machine-readable medium may include any mechanism for storing or transmitting information in a form readable by a machine (e.g., a computer), such as Compact Disc Read-Only Memory (CD-ROMs), Digital Versatile Disc (DVD), Flash Memory, Read-Only Memory (ROMs), Random Access Memory (RAM), and Erasable Programmable Read-Only Memory (EPROM). In other embodiments, some of these operations might be performed by specific hardware components that contain hardwired logic. Those operations might alternatively be performed by any combination of programmable computer components and fixed hardware circuit components.

While the invention has been described in terms of several embodiments, those of ordinary skill in the art will recognize that the invention is not limited to the embodiments described, but can be practiced with modification and alteration within the spirit and scope of the appended claims. The description is thus to be regarded as illustrative instead of limiting. There are numerous other variations to different aspects of the invention described above, which in the interest of conciseness have not been provided in detail. Accordingly, other embodiments are within the scope of the claims.

The invention claimed is:

1. A method for scanning for a second object on or within a first object comprising:

receiving by an electronic circuit included in an adaptive scheduler information associated with the first object and information associated with the second object;

generating by the electronic circuit a first task list including at least one task action based on the information associated with the first object and a second task list including at least one task action based on the information associated with the second object, wherein the at least one task action based on the information associated with the first object includes a first beam firing required for the first object to be scanned and wherein the at least one task action based on the information associated with the second object includes a second beam firing required for the second object to be scanned, wherein the first task list and the second task list respectively include a plurality of task actions that is used for adaptive scheduling, wherein the plurality of task actions include a plurality of parallel ultrasound tasks, wherein each of the ultrasound tasks include a timed beam firing sequence, wherein the plurality of task actions are associated with at least one probe, the at least one probe includes a first probe and a second probe;

adaptively modifying by the electronic circuit the first task list and the second task list based on signals received from an input device or from a signal receiver, wherein the adaptively modifying the first task list or the second task list includes:
determining whether a next task in the first task list or the second task list can be completed without interfering with a start of a higher priority task in the first task list or the second task list; and
modifying a start of the next task in response to determining that the next task cannot be completed without interfering with the start of the higher priority task in the first task list or the second task;

signaling by the electronic circuit based on the first task list to a beamer to generate and send a first signal to the first probe to perform the first beam firing;

receiving and processing by the signal receiver a first data signal from the first probe and sending the processed first data signals to the electronic circuit;

analyzing by the electronic circuit the processed first data signal to determine if the first object is identified using the processed first data signal;

upon determination that the first object is identified using the processed first data signal, signaling by the electronic circuit based on the second task list to the beamer to generate and send a second signal to the second probe to perform the second beam firing;

receiving and processing by the signal receiver a second data signal from the first probe and sending the processed second data signal to the electronic circuit; and analyzing by the electronic circuit the processed second data signal to determine if the second object is identified using the processed second data signal.

2. The method of claim 1, wherein the electronic circuit is a processing element.

3. The method of claim 1, wherein the first object is an organ within a body.

4. The method of claim 1, wherein the second object is an organ within a body.

5. The method of claim 1,
wherein analyzing by the electronic circuit the processed first data signal to determine if the first object is identified using the processed first data signal includes:
determining whether the received information on the first object corresponds to the processed first data signals, and
wherein analyzing by the electronic circuit the processed second data signal to determine if the second object is identified using the processed second data signal includes:
determining whether the received information associated with the second object corresponds to the processed second data signals.

6. The method of claim 1, further comprising:
upon determination that the first object is not identified using the processed first data signal, signaling by the electronic circuit to the beamer to generate and send another first signal to the first probe to perform the first beam firing.

7. The method of claim 1, further comprising:
upon determination that the second object is not identified using the processed first data signal, signaling by the electronic circuit to the beamer to generate and send another second signal to the second probe to perform the second beam firing.

8. The method of claim 1, further comprising:
determining by the electronic circuit whether to adjust the first and second probes.

9. The method of claim 1, further comprising:
updating the first task list based on the analysis of the processed first data signal and the information on the first object, wherein updating the first task list includes adding or deleting tasks actions related to the first beam performing the first beam firing.

10. The method of claim 9, wherein updating the second task list based on the analysis of the processed second data signal and the information on the second object, wherein updating the second task list includes adding or deleting tasks actions related to the second beam performing the second beam firing.

11. The method of claim 1, wherein the first probe is the same as the second probe.

12. The method of claim 1, wherein the first probe is different from the second probe.

13. The method of claim 1, wherein the first and second beam firings are ultrasound beam firings.

14. The method of claim 1, wherein the first task list is the same as the second task list.

15. An apparatus for scanning for a second object on or within a first object comprising:
a processor;
a beamer coupled to the processor to generate a first and a second signal,
a probe interface coupled to the beamer and the processor, the probe interface to transmit the first and second signals to a first probe and a second probe, respectively, and to receive a first data signal and a second data signal, respectively, from the first probe and the second probe, and
a signal receiver coupled to the processor and the probe interface, the signal receiver to receive and process the first data signal and the second data signal received from the probe interface; and
a memory to store instructions, which when executed by the processor, causes the processor:
to receive information associated with the first object and information associated with the second object,
to generate a first task list including at least one task action based on the information associated with the first object and a second task list including at least one task action based on the information associated with the second object, wherein the at least one task action based on the information associated with the first object includes a first beam firing required for the first object to be scanned and wherein the at least one task action based on the information associated with the second object includes a second beam firing required for the second object to be scanned, wherein the first task list and the second task list respectively include a plurality of task actions that is used by the apparatus for adaptive scheduling, wherein the plurality of task actions include a plurality of parallel ultrasound tasks, wherein each of the ultrasound tasks include a timed beam firing sequence, wherein the plurality of task actions are associated with at least one probe, the at least one probe includes the first probe and the second probe, to adaptively modify the first task list and the second task list based on signals received from an input device or from the signal receiver, wherein to adaptively modify the first task list and the second task list, the processor is to
  determine whether a next task in the first task list or the second task list can be completed without interfering with a start of a higher priority task in the first task list or the second task list, and
  modify a start of the next task in response to determining that the next task cannot be completed without interfering with the start of the higher priority task in the first task list or the second task;

to signal by the electronic circuit based on the first task list to the beamer to generate and send the first signal to a first probe to perform the first beam firing, to analyze a processed first data signal to determine if the first object is identified using the processed first data signal, wherein the signal receiver receives and processes the first data signal from the first probe to generate the processed first data signal, upon determination that the first object is identified using the processed first data signal, to signal based on the second task list to the beamer to generate and send a second signal to a second probe to perform the second beam firing, and to analyze by the electronic circuit a processed second data signal to determine if the second object is identified using the processed second data signal, wherein the signal receiver receives and processes a second data signal from the second probe to generate the processed second data signal.

16. The apparatus of claim 15,
wherein analyzing by the processor the processed first data signal to determine if the first object is identified using the processed first data signal includes:
determining whether the received information on the first object corresponds to the processed first data signals, and
wherein analyzing by the processor the processed second data signal to determine if the second object is identified using the processed second data signal includes:
determining whether the received information associated with the second object corresponds to the processed second data signals.

17. The apparatus of claim 15, wherein the memory to store instructions, which when executed by the processor, further causes the processor:
  upon determination that the first object is not identified using the processed first data signal, to signal to the beamer to generate and send another first signal to the first probe to perform the first beam firing.

18. The apparatus of claim 16, wherein the memory to store instructions, which when executed by the processor, further causes the processor:
  upon determination that the second object is not identified using the processed first data signal, to signal to the beamer to generate and send another second signal to the second probe to perform the second beam firing.

19. The apparatus of claim 15, wherein the memory to store instructions, which when executed by the processor, further causes the processor:
  to determine whether to adjust the first and second probes.

20. The apparatus of claim 15, wherein the memory to store instructions, which when executed by the processor, further causes the processor:
  to update the first task list based on the analysis of the processed first data signal and the information on the first object, wherein updating the first task list includes adding or deleting tasks actions related to the first beam performing the first beam firing.

21. The apparatus of claim 20, wherein the memory to store instructions, which when executed by the processor, further causes the processor:
  to update the second task list based on the analysis of the processed second data signal and the information on the second object, wherein updating the second task list includes adding or deleting tasks actions related to the second beam performing the second beam firing.

22. The apparatus of claim 15, wherein the first probe is the same as the second probe.

23. The apparatus of claim 15, wherein the first probe is different from the second probe.

24. The apparatus of claim 15, wherein the first and second beam firings are ultrasound beam firings.

25. The apparatus of claim 15, wherein the first task list is the same as the second task list.

* * * * *